(12) United States Patent
Wang et al.

(10) Patent No.: US 11,959,869 B1
(45) Date of Patent: Apr. 16, 2024

(54) METHOD AND DEVICE FOR MONITORING THE MECHANOCHEMICAL ACTIVATION OF METAL POWDERS IN DYNAMIC ELECTROCHEMICAL ENVIRONMENT

(71) Applicant: Kunming University of Science and Technology, Kunming (CN)

(72) Inventors: Shengmin Wang, Kunming (CN); Chengyu Wang, Kunming (CN); Xiaojun Zhao, Kunming (CN); Peng Liu, Kunming (CN)

(73) Assignee: Kunming University of Science and Technology, Kunming (CN)

( * ) Notice: Subject to any disclaimer, the term of this patent is extended or adjusted under 35 U.S.C. 154(b) by 0 days.

(21) Appl. No.: 18/463,294

(22) Filed: Sep. 8, 2023

(30) Foreign Application Priority Data

Jul. 5, 2023 (CN) .......................... 202310813118.5

(51) Int. Cl.
*G01N 27/30* (2006.01)
*G01N 27/403* (2006.01)
(Continued)

(52) U.S. Cl.
CPC ......... *G01N 27/301* (2013.01); *G01N 27/403* (2013.01); *G01N 27/4146* (2013.01); *G01N 33/208* (2019.01); *G01N 17/02* (2013.01)

(58) Field of Classification Search
CPC .. G01N 27/301; G01N 27/403; G01N 27/416; G01N 27/4166; G01N 27/4167; G01N 17/02
See application file for complete search history.

(56) References Cited

U.S. PATENT DOCUMENTS 6,153,065 A * 11/2000 Yamamoto ............. C25D 17/00
204/224 R
6,251,245 B1 * 6/2001 Satsutani ........... G01N 33/1813
204/408
(Continued)

FOREIGN PATENT DOCUMENTS

CN 1088135 A 6/1994
CN 101520402 A 9/2009
(Continued)

OTHER PUBLICATIONS

'Mechano-chemical reaction' in IUPAC Compendium of Chemical Terminology, 3rd ed. International Union of Pure and Applied Chemistry; 2006. Online version 3.0.1, 2019. https://doi.org/10.1351/goldbook.MTO&141 (Year: 2019).*
(Continued)

*Primary Examiner* — Alexander S Noguerola

(57) ABSTRACT

A method for monitoring mechanochemical activation of metal powders in dynamic electrochemical environment and a device thereof are provided. The method includes constructing a dynamic testing environment in an electrochemical cell, using a three-electrode system, and collecting data from an external electrochemical workstation. The three-electrode system is composed of the working metal plate, the reference electrode, and the platinum electrode. The dynamic testing environment includes small load impacts and changes in pH and composition of the solution. Under the premise of simulating the production environment of the mechanical plating and the water-based metal coating material, the monitoring method described in the present disclosure cooperates with an electrochemical workstation for OCPT testing to achieve the monitoring of mechanochemical activation of metal powders in dynamic electrochemical environment.

8 Claims, 3 Drawing Sheets

(51) Int. Cl.
*G01N 27/414* (2006.01)
*G01N 27/416* (2006.01)
*G01N 33/208* (2019.01)
*G01N 17/02* (2006.01)

(56) References Cited

U.S. PATENT DOCUMENTS

| | | |
|---|---|---|
| 2006/0201814 A1 | 9/2006 | Hafezi |
| 2008/0264795 A1 | 10/2008 | Sides |
| 2015/0167195 A1* | 6/2015 | Sun ............ C25D 17/12 205/83 |
| 2016/0133393 A1 | 5/2016 | Takayasu et al. |
| 2017/0212034 A1 | 7/2017 | Sapper et al. |
| 2020/0220223 A1 | 7/2020 | He et al. |
| 2022/0065813 A1* | 3/2022 | Kyakuno ........... G01N 27/4163 |
| 2022/0099557 A1 | 3/2022 | Asada et al. |

FOREIGN PATENT DOCUMENTS

| | | |
|---|---|---|
| CN | 101627301 A | 1/2010 |
| CN | 102097347 A | 6/2011 |
| CN | 102636531 A | 8/2012 |
| CN | 206052177 U | 3/2017 |
| CN | 106707049 A | 5/2017 |
| CN | 107902791 A | 4/2018 |
| CN | 208642492 U | 3/2019 |
| CN | 110470722 A | 11/2019 |
| CN | 110658128 A | 1/2020 |
| CN | 111788478 A | 10/2020 |
| CN | 111855792 A | 10/2020 |
| CN | 211760249 U | 10/2020 |
| CN | 214490086 U | 10/2021 |
| CN | 115825179 A | 3/2023 |
| JP | 2005035034 A | 2/2005 |
| JP | 2022001834 A | 1/2022 |

OTHER PUBLICATIONS

«Chinese Journal of Mechanical Engineering» vol. 22, issue 4;Aug. 1, 2009; Wang, SM et al, "Microstructures and Key Properties of Mechanically Deposited Zn—Al Coatings" p. 608-613.

«Acta Physica Polonica A» vol. 135, issue 5; Sep. 4, 2019; Mindivan, H, "Tribocorrosion Behaviour of Electroless Ni—P Coating on AA7075 Aluminum Alloy" p. 1102-1104.

«Materials Science & Technology» issue 5; Aug. 15, 2008; Wang Shengmin et al "Mechanism of mechanical deposition in mechanical plating" p. 535-538.

«T r ansactions of Mate r ials and Heat T r eatment» vol. 37, issue 3; Mar. 25, 2016; Liu Huawei et al "Microstructure and electrochemical properties of mechanically deposited zinc diffusion coating" p. 176-180.

«Nanfang Agricultural Machinery» vol. 49, issue 3; Feb. 15, 2018; Liu Linli et al "Research status of mechanical plating" p. 157+160.

* cited by examiner

METHOD AND DEVICE FOR MONITORING THE MECHANOCHEMICAL ACTIVATION OF METAL POWDERS IN DYNAMIC ELECTROCHEMICAL ENVIRONMENT

TECHNICAL FIELD

The present disclosure relates to the field of electrochemical experimental monitoring technology, in particular to a method for monitoring mechanochemical activation of metal powders in dynamic electrochemical environment and a device thereof.

BACKGROUND

Corrosion is a common problem in the steel industry, which not only affects the quality of steel materials, shortens service life of steel materials, but also causes pollution to the natural environment. At present, the commonly used anti-corrosion treatment methods for steel materials include hot-dip galvanization and electro galvanizing, but these processes inevitably produce harmful substances such as waste gas, waste liquid, waste residue, etc. in the production process. Relatively speaking, mechanical plating and water-based metal powder coating material technology have environmental advantages of low pollution or even no pollution while providing excellent anti-corrosion effects. The current research and production practice indicate that whether metal powder can be continuously and stably adsorbed and deposited on the steel substrate during the mechanical plating process is the primary factor determining whether metal powder can form a coating material; whether the metal powder in the water-based metal powder coating material can be evenly dispersed in a short period of time and undergo a certain degree of low-temperature sintering during coating material is a key link that affects whether the metal powder can form a film and ensure sufficient bonding strength. These require effective activation and stable control of the surface of metal powder to ensure the reaction and solid bonding between particles during the coating material or film formation process of metal powder. The activation of metal powders includes chemical activation and mechanochemical reactions. The changes and patterns of surface potential of metal powders during activation are directly related to various chemical and mechanochemical reactions. However, there is currently a lack of effective methods and devices for monitoring the activation process of metal powders in relevant technical fields.

Open circuit potential (OCP) refers to the difference in potential measured between the sample and the reference electrode when no external potential is applied. By measuring the change of open circuit potential-time (OCPT), the change of surface states of the measured object can be known. However, a single electrochemical workstation can only measure the OCPT of the sample in a stable environment, which cannot meet the demand for measuring the open circuit potential value of the working electrode that tends to stabilize in a dynamic electrochemical environment. Therefore, data is difficult to directly apply to industrial production and practical applications. The mechanical plating process and the coating material process of water-based metal micro powder coating material are dynamic reactions. The activation of metal powder involves chemical and mechanochemical reactions, the current electrochemical workstation cannot measure the data of various metal powders under working conditions or near working conditions, nor can it directly conduct and regulate surface activation of metal powders. In addition, the existing electrochemical measurement devices have a simple structure and are only suitable for testing in static liquid environments. The sample preparation steps are cumbersome, and each electrode needs to be disassembled and maintained, resulting in complex operations. Therefore, the study of a method and device that can achieve the mechanochemical activation and regulation of the surface of metal powders is an urgent problem in the related technical field.

SUMMARY

The main objective of the present disclosure is to provide a method and a device for monitoring the mechanochemical activation of metal powders in dynamic electrochemical environment. The monitoring method described in the present disclosure enables the monitoring of the correlation of changes in surface potential with changes in the dynamic test environment when mechanochemical activation of metal powders occurs. At the same time, the device of the present disclosure solves the problem that existing electrochemical workstations can only measure OCPT in a stable environment, as well as the problem of difficult control of distance between electrodes and low testing efficiency caused by frequent electrode replacement.

To realize the above objective, a method for monitoring the mechanochemical activation of metal powders in dynamic electrochemical environment is provided by the present disclosure, wherein the method includes: constructing a dynamic testing environment in an electrochemical cell, using a three-electrode system, and collecting data from an external electrochemical workstation; the three-electrode system is composed of the working metal plate 11, the reference electrode 23, and the platinum electrode 24; and the construction of the dynamic testing environment includes the following steps:

S1: injecting the impact medium and water into the electrochemical cell 5, with a water level higher than that of the impact medium;

S2: detachably connecting an upper end of the first electrode 14 on the upper part of the replaceable material electrode 1 to the connecting piece 41 on the lower part of the rotating mechanism 4, so that the rotating mechanism 4 drives the replaceable material electrode 1 to rotate, causing the working metal plate 11 on the lower end of the replaceable material electrode 1 to collide with the impact medium, and collecting OCPT data from the electrochemical workstation;

S3: adding acid or alkali to the electrochemical cell 5 and continuously collecting data from the electrochemical workstation; then adding active agents and continuously collecting data from the electrochemical workstation; finally, adding the metal powders and continuously collecting data from the electrochemical workstation.

The present disclosure simulates the production environment of the mechanical plating and the water-based metal coating material, and cooperates with an electrochemical workstation for OCPT testing to achieve the monitoring of mechanochemical activation of metal powders in dynamic electrochemical environment. The dynamic testing environment includes small load impacts and changes in pH and composition of the solution.

As a further improvement of the present disclosure, the material of the working metal plate 11 is one of metal iron, zinc, magnesium, aluminum, titanium, platinum, silver, copper, tin, gold or nickel. The impact medium are glass beads.

The acid and alkali active agents, and metal powder are common medicines and chemical reagents in this field. The present disclosure explores the activation effect of acid and alkali active agents on the surface of metal powders and working metal plate 11 through the above monitoring method. Therefore, acid and alkali active agents, and metals are not specific, and common medicines and chemical reagents in this field can be used to detect whether they have activation effect on metal powders and working metal plate 11.

Further, A device for monitoring mechanochemical activation of metal powders in dynamic electrochemical environment is provided by the present disclosure, including a casing 7, a rotating mechanism 4, a replaceable material electrode 1, an adjustable electrode holder 2, and an electrochemical cell 5.

A top of the casing 7 is provided with the rotating mechanism 4, and a bottom of of the casing is provided with the electrochemical cell 5; the rotating mechanism 4 is detachably connected to an upper end of a first electrode 14 on an upper part of the replaceable material electrode 1 through a connecting piece 41, configured to drive the replaceable material electrode 1 to rotate as a whole.

The electrochemical cell 5 is provided with the replaceable material electrode 1, a platinum electrode 24, and a reference electrode 23.

A lower end of the replaceable material electrode 1 is connected to the working metal plate 11; the replaceable material electrode 1 extends into the electrochemical cell 5 and is perpendicular to a bottom of the electrochemical cell 5; and the working metal plate 11 is in contact with liquid and impact medium in the electrochemical cell 5.

The platinum electrode 24 and the reference electrode 23 are fixed by an adjustable electrode holder 2; and the adjustable electrode holder 2 is movably arranged on one side of the casing 7 and is capable of being adjusted up and down.

The replaceable material electrode 1, the reference electrode 23, and the platinum electrode 24 are respectively connected to the electrochemical workstation through a first working electrode conduction circuit 81, a first reference electrode conduction circuit 82, and a first platinum electrode conduction circuit 83.

As a further improvement of the present disclosure, the working electrode conductive post, the reference electrode conductive post, and the platinum electrode conductive post are arranged on the outer surface of the right side of the casing 7. One end of the first working electrode conductive circuit 81 is connected to the working electrode conductive post, and the other end is fixedly connected to the copper brush 3. The copper brush 3 is slidably connected to the sliding conductive post 13, and the copper brush 3 is used for conducting the working electrode circuit. One end of the first reference electrode conduction circuit 82 is connected to the reference electrode conductive post, and the other end is slidably connected to the reference electrode conduction circuit sliding groove 27 for the conduction of the reference electrode circuit. One end of the first platinum electrode conduction circuit 83 is connected to the platinum electrode conductive post, and the other end is slidably connected to the platinum electrode conduction circuit sliding groove 28 for the conduction of the platinum electrode circuit.

As a further improvement of the present disclosure, the materials of the first working electrode conduction circuit 81, the first reference electrode conduction circuit 82, the first platinum electrode conduction circuit 83, the working electrode conduction post, the reference electrode conduction post, and the platinum electrode conduction post are brass.

As a further improvement of the present disclosure, the electrochemical cell 5 is a double-layer water bath electrochemical cell, which has the functions of heat preservation and temperature control.

As a further improvement of the present disclosure, the adjustable electrode holder 2 includes two electrode mounting pieces arranged in parallel and a clamping piece, the clamping piece is clamped on one side of the casing 7, and the two electrode mounting pieces are configured for installing the platinum electrode 24 and the reference electrode 23, respectively.

As a further improvement of the present disclosure, each of the two electrode mounting pieces is provided with electrode mounting holes 25 distributed in a linear array, and the number of the electrode mounting holes 25 on each electrode mounting piece is at least two.

More preferably, the number of the electrode mounting holes on each electrode mounting piece is 4, which facilitates the compatibility of electrochemical cells of different sizes.

As a further improvement of the present disclosure, the reference electrode 23, the platinum electrode 24 are fixedly connected with the electrode mounting holes 25.

More preferably, the inner surface of each electrode mounting hole 25 is equipped with internal threads. The external surfaces of the reference electrode 23 and the platinum electrode 24 are equipped with matching external threads, and the reference electrode 23 and the platinum electrode 24 are screwed into the internal threads through the external threads to fix the electrode in the electrode mounting holes 25.

As a further improvement of the present disclosure, an inner surface of the clamping piece in contact with the casing 7 is provided with a reference electrode conduction circuit sliding groove 27 and a platinum electrode conduction circuit sliding groove 28; one side of the casing 7 is provided with the first working electrode conduction circuit 81 and the first reference electrode conduction circuit 82, and the first platinum electrode conduction circuit 83; the clamping piece moves up and down along a direction of the first reference electrode conduction circuit 82 and the first platinum electrode conduction circuit 83; the reference electrode conduction circuit sliding groove 27 and the platinum electrode conduction circuit sliding groove 28 respectively slide in contact with the first reference electrode conduction circuit 82 and the first platinum electrode conduction circuit 83 to achieve circuit connection; the reference electrode conduction circuit sliding groove 27 is connected to the reference electrode 23 through the second reference electrode conduction circuit 21, and the platinum electrode conduction circuit sliding groove 28 is connected to the platinum electrode 24 through the second platinum electrode conduction circuit 22.

As a further improvement of the present disclosure, the lengths of the reference electrode conduction circuit sliding groove 27 and the platinum electrode conduction circuit sliding groove 28 are the same as the thickness of the first clamp plate.

As a further improvement of the present disclosure, a second reference electrode conduction circuit 21 and a second platinum electrode conduction circuit 22 are attached to an upper surface of the clamping piece.

As a further improvement of the present disclosure, the clamping piece includes a U-shaped cavity composed of a first clamp plate and a second clamp plate. The middle end of the second clamp plate on the other side away from the U-shaped cavity is provided with threads to connect with the fixing bolt 26. The upper end of the second clamp plate on the other side away from the U-shaped cavity is equipped with two electrode mounting pieces in parallel.

As a further improvement of the present disclosure, the first clamp plate and the second clamp plate are integrated or fixedly connected to form a U-shaped cavity.

More preferably, the first clamp plate and the second clamp plate are integrated as a whole.

As a further improvement of the present disclosure, the second reference electrode conduction circuit 21 and the second platinum electrode conduction circuit 22 are attached to an upper surface of the clamping piece.

As a further improvement of the present disclosure, there is no short circuit in the second reference electrode conduction circuit 21 and the second platinum electrode conduction circuit 22.

As a further improvement of the present disclosure, the fixing bolt 26 does not interfere with other components of the adjustable electrode holder 2. The tightening of the fixing bolt 26 is adjusted to determine whether the adjustable electrode holder 2 can slide.

As a further improvement of the present disclosure, the material of the second reference electrode conduction circuit 21 and the second platinum electrode conduction circuit 22 is copper wire.

As a further improvement of the present disclosure, the replaceable material electrode 1 includes a second electrode 12, a sliding conductive post 13, the first electrode 14, and a copper core 16; a lower end of the second electrode 12 is provided with a through groove, and the working metal plate 11 is fixed in the through groove at the lower end of the second electrode 12 to form an exposed part; one end of the sliding conductive post 13 is connected to the first electrode 14, and the other end is connected to the second electrode 12; an inner center of the second electrode 12 is provided with the copper core 16, and the copper core is connected to the working metal plate 11 and the sliding conductive post 13.

The lower end of the second electrode 12 is equipped with a through groove, and the cross-sectional size of the through groove opening is consistent with the cross-sectional area of the working metal plate 11. There is a gap between the bottom surface of the through groove and the bottom surface of the second electrode 12 that is perpendicular to both sides and in the same direction as the through groove. The working metal plate 11 is pushed into the through groove, and when the center point of the long side of the working metal plate 11 coincides with the second electrode 12, stopping the pushing. The non overlapping part of the working metal plate 11 and the through groove forms the exposed part.

More preferably, the sidewall of the gap of the through groove is horizontally provided with a threaded hole that runs through the center of the side wall. The fixing screw 15 passes through the corresponding two threaded holes and is connected to the threaded holes through threads, clamping and fixing the working metal plate 11 in the through groove.

As a further improvement of the present disclosure, the sliding conductive post 13 is connected to the first working electrode conduction circuit 81 through an electric brush 3.

As a further improvement of the present disclosure, one end of the sliding conductive post 13 is fixedly connected to the first electrode 14, and the other end of the sliding conductive post 13 is fixedly connected to the second electrode 12.

More preferably, the upper end of the second electrode 12 is equipped with external threads, the two ends of the sliding conductive post 13 are equipped with internal threads, and the lower end of the second electrode 14 is equipped with external threads. The upper end of the second electrode 12 is threaded to the lower end of the sliding conductive post 13, and the upper end of the sliding conductive post 13 is threaded to the lower end of the first electrode 14.

As a further improvement of the present disclosure, the material of the second electrode 12 is plastic. The material of the sliding conductive post 13 is brass. The material of the first electrode 14 is plastic. The material of the copper core 16 is pure copper.

As a further improvement of the present disclosure, the rotating mechanism 4 includes a connecting piece 41, a rotating mechanism speed signal input port 42, and a rotating mechanism power interface 43.

As a further improvement of the present disclosure, the rotating mechanism 4 is a low-speed motor, and the connecting piece 41 is a spin chuck.

As a further improvement of the present disclosure, the lifting platform 6 is equipped with a fixed switch 61 for locking the lifting platform 6, and the lifting platform 6 is used to change the height of the electrochemical cell 5.

As a further improvement of the present disclosure, the electrochemical cell 5 is used to hold impact medium, aqueous solutions, and active agents.

As a further improvement of the present disclosure, the casing 7 is non conductive plastic.

The advantageous effects of the present disclosure are shown as below:

(1) Under the premise of simulating the production environment of the mechanical plating and the water-based metal coating material, the monitoring method described in the present disclosure cooperates with an electrochemical workstation for OCPT testing to achieve the monitoring of mechanochemical activation of metal powders in dynamic electrochemical environment. It represents the surface changes of metal powder materials in the micro-environment in a digital form, facilitating the development and activation identification of the mechanical plating and the water-based metal coating material.

(2) The present disclosure provides a device for monitoring the mechanochemical activation of metal powders in dynamic electrochemical environment. By modifying the working electrode and electrode holder, a dynamic testing environment with adjustable impact load, solution environment, and testing temperature is constructed to monitor the correlation of changes in surface potential with changes in the dynamic test environment when mechanochemical activation of metal powders occurs. At the same time, the device of the present disclosure assists the electrochemical workstation to carry out a series of electrochemical tests to standardize the working environment for electrochemical testing, such as the fixing of electrode distance and the setting of test temperature. In addition, there is no need for complex sample preparation and tedious replacement of test samples, which simplifies the installation, maintenance and operation of electrodes, improves the efficiency of electrochemical testing overall, and has good compatibility with various electrochemical cells.

ILLUSTRATIONS OF LABELS IN ATTACHED DRAWING

Figure 1:
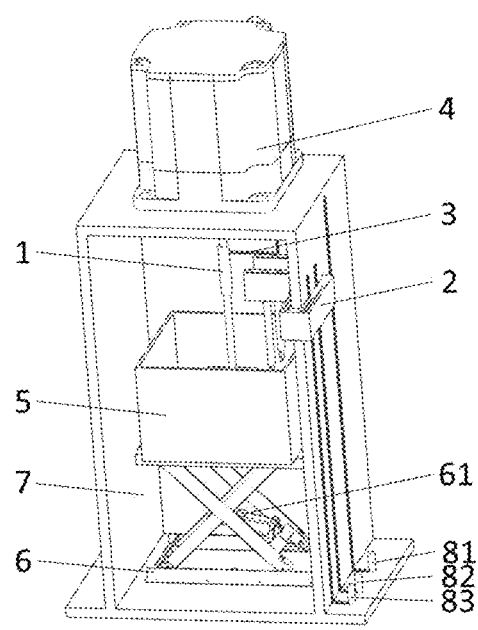
FIG. 1 is a front view schematic diagram showing of the structure of the device for monitoring mechanochemical activation of metal powders in dynamic electrochemical environment as described in the present disclosure.
Figure 2:
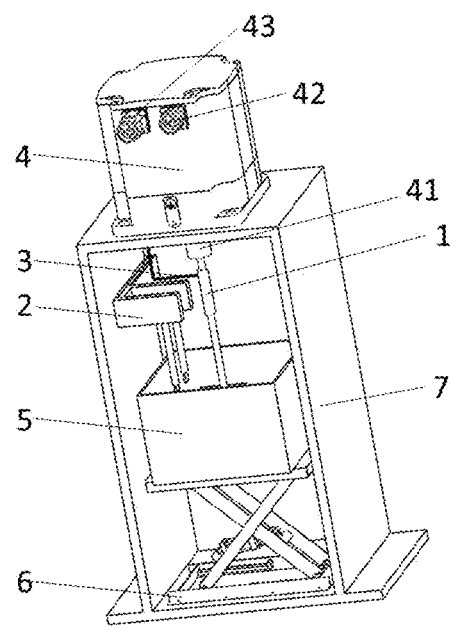
FIG. 2 is a rear view schematic diagram showing of the structure of the device for monitoring mechanochemical activation of metal powders in dynamic electrochemical environment as described in the present disclosure.
Figure 3:
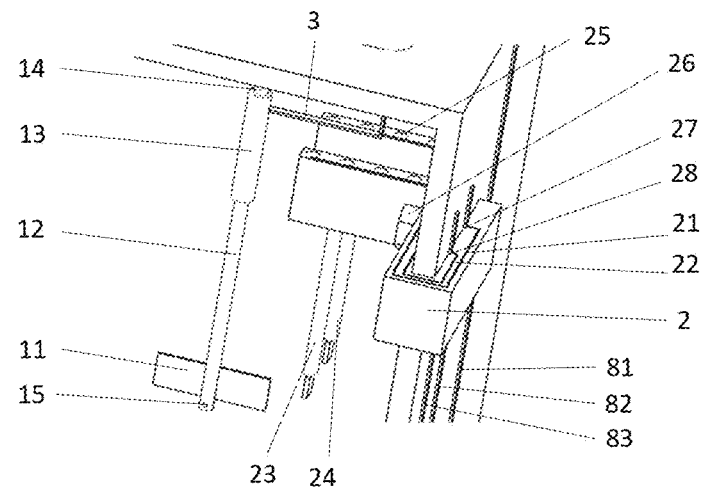
FIG. 3 is a schematic diagram of the local structure of the device for monitoring mechanochemical activation of metal powders in dynamic electrochemical environment as described in the present disclosure.
Figure 4:
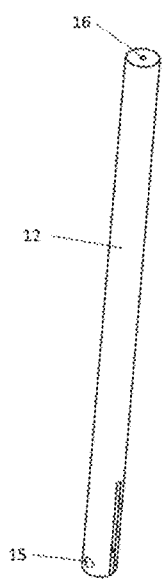
FIG. 4 is a schematic diagram showing of the structure of the second electrode, the copper core, and the fixing screw of the replaceable material electrode device according to the present disclosure.
Figure 5:
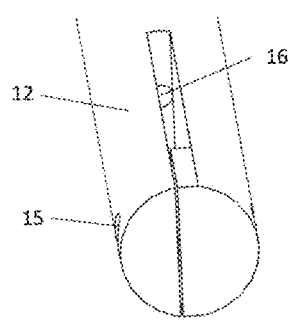
FIG. 5 is a schematic diagram of the local structure of the replaceable material electrode device of the present disclosure.

1—replaceable material electrode, 11—working metal plate, 12—the second electrode, 13—sliding conductive post, 14—the first electrode, 15—fixing screw, 16—copper core, 2—adjustable electrode holder, 21—the second reference electrode conduction circuit, 22—the second platinum electrode conduction circuit, 23—reference electrode, 24—platinum electrode, 25—electrode installation hole, 26—fixing bolt, 27—reference electrode conduction circuit sliding groove, 28—platinum electrode conduction circuit sliding groove, 3—copper brush, 4—rotating mechanism, 41—connecting piece, 42—rotating mechanism speed signal input port, 43—rotating mechanism power interface, 5—electrochemical cell, 6—lifting platform, 61—fixed switch of lifting platform, 7—casing, 81—the first working electrode conduction circuit, 82—the first reference electrode conduction circuit, 83—the first platinum electrode conduction circuit.

DETAILED DESCRIPTION OF THE EMBODIMENTS

In order to make the objective, technical solution, and advantages of the present disclosure clearer, the following will provide a further detailed illustration of the present disclosure in conjunction with the accompanying drawings and embodiments. It should be understood that the described embodiments are only some of the embodiments of the present disclosure, not all of them. Without conflict, the embodiments in this application and the features in the embodiments can be combined with each other. Based on the embodiments in the present disclosure, all other embodiments obtained by ordinary skilled person in the art without creative labor fall within the scope of the present disclosure.

Embodiment 1

The device used for monitoring the mechanochemical activation of metal powders in dynamic electrochemical environment, as shown in FIGS. 1-5, includes:

A casing 7, a rotating mechanism 4, a replaceable material electrode 1, an adjustable electrode holder 2, and an electrochemical cell 5.

The lifting platform 6 is fixed at the bottom inside the casing 7, and is used to change the height of the electrochemical cell 5. The lifting platform 6 is equipped with a fixed switch 61 for locking the lifting platform 6. The electrochemical cell 5 is placed directly above the lifting platform 6. The electrochemical cell 5 is used to hold impact medium, aqueous solutions, acids, active agents, and metal powders. The casing 7 is non conductive plastic.

The rotating mechanism 4 is fixed directly above the casing 7, and the rotating mechanism 4 is used to drive the replaceable material electrode 1. The rotating mechanism 4 includes a connecting piece 41, a rotating mechanism speed signal input port 42, and a rotating mechanism power interface 43. The rotating mechanism speed signal input port 42 is used to change the speed of the replaceable material electrode 1, and the rotating mechanism power interface 43 is used to supply power to the rotating mechanism 4. The connecting piece 41 at the lower end of the rotating mechanism 4 runs through the casing 7 and is clamped and fixed with the upper end of the first electrode 14 on the upper part of the replaceable material electrode 1. The replaceable material electrode 1 is located directly above the electrochemical cell 5. The replaceable material electrode 1 extends into the electrochemical cell 5 and is perpendicular to a bottom of the electrochemical cell 5, and the working metal plate 11 connected to the lower end of the replaceable material electrode 1 is in contact with the solution in the electrochemical cell 5.

The adjustable electrode holder 2 is fixed to the right casing of the casing 7 through a U-shaped cavity structure of the clamping piece. The inner surface of the U-shaped cavity is equipped with the reference electrode conduction circuit sliding groove 27 and platinum electrode conduction circuit sliding groove 28 which are in parallel. The adjustable electrode holder 2 moves up and down through a component composed of the reference electrode conduction circuit sliding groove 27 and the platinum electrode conduction circuit sliding groove 28, so as to insert the platinum electrode 24 and the reference electrode 23 held on the adjustable electrode holder 2 into the inner cavity of the electrochemical cell 5.

The first working electrode conduction circuit 81, the first reference electrode conduction circuit 82, and the first platinum electrode conduction circuit 83 are attached to the outer surface on the right side of the casing 7. The working electrode conductive post, the reference electrode conductive post, and the platinum electrode conductive post are arranged on the outer surface of the right side of the casing 7. One end of the first working electrode conductive circuit 81 is connected to the working electrode conductive post, and the other end is fixedly connected to the copper brush 3. The copper brush 3 is slidably connected to the sliding conductive post 13, and the copper brush 3 is used for conducting the working electrode circuit. One end of the first reference electrode conduction circuit 82 is connected to the reference electrode conductive post, and the other end is slidably connected to the reference electrode conduction circuit sliding groove 27. One end of the first platinum electrode conduction circuit 83 is connected to the platinum electrode conductive post, and the other end is slidably connected to the platinum electrode conduction circuit sliding groove 28. The reference electrode conductive post, the first reference electrode conductive circuit 82, and the reference electrode conduction circuit sliding groove 27 are conductive to the second reference electrode conductive circuit 21. The platinum electrode conductive post, the first platinum electrode conductive circuit 83, and the platinum electrode conduction circuit sliding groove 28 are conductive to the second platinum electrode conductive circuit 22. Through a component composed of the reference electrode conduction circuit sliding groove 27 and the platinum electrode conduction circuit sliding groove 28, the adjustable electrode holder 2 slides up and down on the guide rail composed of the first reference electrode conduction circuit 82 and the first platinum electrode conduction circuit 83, which are attached to the outer surface of the right side of the casing 7. The materials of the first working electrode conduction circuit 81, the first reference electrode conduction circuit 82, the first platinum electrode conduction circuit 83, the working electrode conduction post, the reference electrode conduction post, and the platinum electrode conduction post are brass.

More preferably, the first working electrode conduction circuit 81, the first reference electrode conduction circuit 82, and the first platinum electrode conduction circuit 83 do not cross contact with each other.

More preferably, the replaceable material electrode 1 includes a second electrode 12, a sliding conductive post 13, the first electrode 14, a fixing screw 15, and a copper core 16. The center of the second electrode 12 is equipped with the copper core 16, which is used for conducting the circuit between the working metal plate 11 and the sliding conductive post 13. A lower end of the second electrode 12 is provided with a through groove, and the working metal plate 11 is inserted into the through groove at the lower end of the second electrode 12 to form an exposed part arranged symmetrically. The two sides of the lower gap of the through groove is horizontally provided with threaded holes that run through the side wall. The fixing screw 15 passes through the corresponding two threaded holes and is connected to the threaded holes through threads, clamping and fixing the working metal plate 11 in the through groove. The upper end of the second electrode 12 is equipped with external threads, the two ends of the sliding conductive post 13 are equipped with internal threads, and the lower end of the second electrode 14 is equipped with external threads. The upper end of the second electrode 12 is threaded to the lower end of the sliding conductive post 13, and the upper end of the sliding conductive post 13 is threaded to the lower end of the first electrode 14. The working metal plate 11 is made of metal iron. The material of the second electrode 12 is plastic. The material of the sliding conductive post 13 is brass. The material of the first electrode 14 is plastic. The material of the copper core 16 is pure copper.

More preferably, the lower end of the second electrode 12 is equipped with a through groove, and the cross-sectional size of the through groove opening is consistent with the cross-sectional area of the working metal plate 11. There is a gap between the bottom surface of the through groove and the bottom surface of the second electrode 12 that is perpendicular to both sides and in the same direction as the through groove. The working metal plate 11 is pushed into the through groove, and when the center point of the long side of the working metal plate 11 coincides with the second electrode 12, stopping the pushing. The non overlapping part of the working metal plate 11 and the through groove forms the exposed part.

More preferably, the sidewall of the gap of the through groove is horizontally provided with a threaded hole that runs through the center of the side wall. The fixing screw 15 passes through the corresponding two threaded holes and is connected to the threaded holes through threads, clamping and fixing the working metal plate 11 in the through groove.

The adjustable electrode holder 2 includes a second reference electrode conduction circuit 21, a second platinum electrode conduction circuit 22, a reference electrode 23, a platinum electrode 24, electrode mounting holes 25, a fixing bolt 26 of the electrode holder, a reference electrode conduction circuit sliding groove 27, a platinum electrode conduction circuit sliding groove 28, and a clamping piece. The clamping piece includes a U-shaped cavity composed of a first clamp plate and a second clamp plate. The middle end of the second clamp plate on the other side away from the U-shaped cavity is provided with threads to connect with the fixing bolt 26. The tightening of the fixing bolt 26 is adjusted to determine whether the adjustable electrode holder 2 can slide. The upper end of the second clamp plate on the other side away from the U-shaped cavity is equipped with two electrode mounting pieces in parallel. The two electrode mounting pieces are respectively equipped with the electrode mounting holes 25. The inner surface of each electrode mounting hole 25 is equipped with internal threads. The external surfaces of the reference electrode 23 and the platinum electrode 24 are equipped with matching external threads, and the reference electrode 23 and the platinum electrode 24 are screwed into the internal threads through the external threads to fix the electrode in the electrode mounting holes 25. The second reference electrode conduction circuit 21 and the second platinum electrode conduction circuit 22 are attached to an upper surface of the clamping piece. The two ends of the second reference electrode conduction circuit 21 are respectively connected to the reference electrode 23 and the reference electrode conduction circuit sliding groove 27, while the two ends of the second platinum electrode conduction circuit 22 are respectively connected to the platinum electrode 24 and the platinum electrode conduction circuit sliding groove 28.

In the present embodiment, the number of the electrode mounting holes 25 on each electrode mounting piece is 4, the electrode mounting holes 25 on each electrode mounting piece are distributed in a linear array, which facilitate the compatibility of electrochemical cells of different sizes.

More preferably, the lengths of the reference electrode conduction circuit sliding groove 27 and the platinum electrode conduction circuit sliding groove 28 are the same as the thickness of the first clamp plate.

More preferably, there is no short circuit in the second reference electrode conduction circuit 21 and the second platinum electrode conduction circuit 22. The material of the second reference electrode conduction circuit 21 and the second platinum electrode conduction circuit 22 is copper wire.

Embodiment 2

A method for monitoring the mechanochemical activation of metal powders in dynamic electrochemical environment includes the following steps:

(1) Connecting electrode clamps with the electrochemical workstation: green clamp clamps the conductive post of the working electrode conductive post, white clamp clamps the reference electrode conductive post, and red clamp clamps the platinum electrode conductive post;

(2) Installing the reference electrode 23, the platinum electrode 24, and the working metal plate 11: S1: screwing the reference electrode 23 and the platinum electrode 24 into the inner surface threads of the electrode mounting holes 25 through the external threads, and fixing the reference electrode 23 and the platinum electrode 24 in different the electrode mounting holes 25; S2: inserting the working metal plate 11 into the through groove at the lower end of the second electrode 12 to form a symmetrical exposed part; screwing the fixing screw 15 through the threaded holes on both sides of the lower gap of the through groove to connect with the threaded holes through threads; fixing the working metal plate 11 in the through groove; connecting the upper end of the second electrode 12 to the lower end of sliding conductive post 13 through threads, and connecting the upper end of sliding conductive post 13 to the lower end of the first electrode 14 through threads; and connecting the sliding conductive post 13 to the copper brush 3 in a sliding manner.

(3) Adding 300 ml of glass beads and 500 ml of water to the electrochemical cell 5 in sequence;

(4) adjusting the height of the lifting platform 6 to ensure that the working area of the working metal plate 11 is submerged in the glass beads; pressing the fixed switch 61 to fix the height of the electrochemical cell 5; the adjustable electrode holder 2 slides along the guide rail composed of the first reference electrode conduction circuit 82 and the first platinum electrode conduction circuit 83 attached to the outer surface of the right side of the casing 7, so that the working area of the reference electrode 23 and the platinum electrode 24 are submerged in water, but do not contact the glass beads, and then tightening the fixing bolt 26 to fix the adjustable electrode holder 2.

(5) clamping and fixing the upper end of the first electrode 14 on the top of the replaceable material electrode 1 with the connection piece 41 at the lower end of the rotating mechanism 4; then connecting the rotating mechanism power interface 43, connecting the rotating mechanism speed signal input port 42, and adjusting the rotational speed of the rotating mechanism 4 to 180 r/min, so that the working metal plate 11 on the replaceable material electrode 1 undergoes a mechanochemical reaction with the glass beads; applying a computer program to collect OCPT data from the electrochemical workstation;

(6) adding sulfuric acid, and continuing to collect data from the electrochemical workstation, observing the changes in OCPT data; then adding stannous sulfate, continuing to collect data from the electrochemical workstation, and observing the changes of OCPT data; finally, adding zinc powders, and continuing to collect data from the electrochemical workstation, observing the changes in OCPT data.

(7) disconnecting the power supply of the rotating mechanism 4 after completion, analyzing OCPT data, observing the surface condition of working metal plate 11 and the morphology of metal powders in the electrochemical cell 5, and collecting them for comprehensive analysis of activation effect.

The working metal plate 11 in this embodiment is an iron plate.

Figure 6:
FIG. 6 is a photo picture of the zinc coating material formed on the surface of the working metal plate in Embodiment 1 of the present disclosure after testing.

This embodiment observed certain fluctuations in OCPT data, with the open circuit potential of iron shifting negatively to the potential of zinc. According to FIG. 6, the left side shows the original working metal plate 11, and the right side shows the working metal plate 11 after mechanochemical activation. It can be seen that the surface of the working metal plate 11 is impacted by glass beads to form a zinc coating material, and the metal powders in electrochemical cell 5 is observed to form clusters and collected. The comprehensive analysis shows that it has certain activation effect on zinc powder, sulfuric acid and stannous sulfate, which are suitable for auxiliary addition in mechanical plating production.

The above is only preferred embodiments of the present disclosure and is not intended to limit it. Any modifications, equivalent substitutions, improvements, etc. made within the spirit and principles of the present disclosure should be included in the scope of the present disclosure.

What is claimed is:

1. A device for monitoring mechanochemical activation of metal powders in dynamic electrochemical environment, comprising a casing (7), a rotating mechanism (4), a replaceable material electrode (1), an adjustable electrode holder (2), and an electrochemical cell (5),
   wherein a top of the casing (7) is provided with the rotating mechanism (4), and a bottom of the casing is provided with the electrochemical cell (5); the rotating mechanism (4) is detachably connected to an upper end of a first electrode (14) on an upper part of the replaceable material electrode (1) through a connecting piece (41), configured to drive the replaceable material electrode (1) to rotate as a whole;
   the electrochemical cell (5) is provided with the replaceable material electrode (1), a platinum electrode (24), and a reference electrode (23);
   a lower end of the replaceable material electrode (1) is connected to a working metal plate (11); the replaceable material electrode (1) extends into the electrochemical cell (5) and is perpendicular to a bottom of the electrochemical cell (5); the working metal plate (11) is in contact with liquid and glass beads in the electrochemical cell (5);
   the platinum electrode (24) and the reference electrode (23) are fixed by an adjustable electrode holder (2); the adjustable electrode holder (2) is movably arranged on one side of the casing (7) and is capable of being adjusted up and down;
   the replaceable material electrode (1), the reference electrode (23), and the platinum electrode (24) are respectively connected to an electrochemical workstation through a first working electrode conduction circuit (81), a first reference electrode conduction circuit (82), and a first platinum electrode conduction circuit (83).

2. The device for monitoring the mechanochemical activation of metal powders in dynamic electrochemical environment according to claim 1, wherein the adjustable electrode holder (2) comprises two electrode mounting pieces arranged in parallel and a clamping piece, the clamping piece is clamped on one side of the casing (7), and the two electrode mounting pieces are configured for installing the platinum electrode (24) and the reference electrode (23), respectively.

3. The device for monitoring the mechanochemical activation of metal powders in dynamic electrochemical environment according to claim 2, wherein each of the two electrode mounting pieces is provided with electrode mounting holes (25) distributed in a linear array, and the number of the electrode mounting holes (25) on each electrode mounting piece is at least two.

4. The device for monitoring the mechanochemical activation of metal powders in dynamic electrochemical environment according to claim 2, wherein an inner surface of the clamping piece in contact with the casing (7) is provided with a reference electrode conduction circuit sliding groove (27) and a platinum electrode conduction circuit sliding groove (28); one side of the casing (7) is provided with the first working electrode conduction circuit (81) and the first reference electrode conduction circuit (82), and the first platinum electrode conduction circuit (83); the clamping piece moves up and down along a direction of the first reference electrode conduction circuit (82) and the first platinum electrode conduction circuit (83); the reference electrode conduction circuit sliding groove (27) and the platinum electrode conduction circuit sliding groove (28) respectively slide in contact with the first reference electrode conduction circuit (82) and the first platinum electrode conduction circuit (83) to achieve circuit connection; the reference electrode conduction circuit sliding groove (27) is connected to the reference electrode (23) through the second reference electrode conduction circuit (21), and the platinum electrode conduction circuit sliding groove (28) is connected to the platinum electrode (24) through the second platinum electrode conduction circuit (22).

5. The device for monitoring the mechanochemical activation of metal powders in dynamic electrochemical environment according to claim 4, wherein a second reference electrode conduction circuit (21) and a second platinum electrode conduction circuit (22) are attached to an upper surface of the clamping piece.

6. The device for monitoring the mechanochemical activation of metal powder in dynamic electrochemical environment according to claim 1, wherein the replaceable material electrode (1) comprises a second electrode (12), a sliding conductive post (13), the first electrode (14), and a copper core (16); a lower end of the second electrode (12) is provided with a through groove, and the working metal plate (11) is fixed in the through groove at the lower end of the second electrode (12) to form an exposed part; one end of the sliding conductive post (13) is connected to the first electrode (14), and the other end is connected to the second electrode (12); an inner center of the second electrode (12) is provided with the copper core (16), and the copper core is connected to the working metal plate (11) and the sliding conductive post (13).

7. The device for monitoring the mechanochemical activation of metal powders in a dynamic electrochemical environment according to claim 6, wherein the sliding conductive post (13) is connected to the first working electrode conduction circuit (81) through an electric brush (3).

8. The device for monitoring the mechanochemical activation of metal powders in dynamic electrochemical environment according to claim 1, wherein a lifting platform (6) is placed at a bottom of the casing (7), and the electrochemical cell (5) is placed directly above the lifting platform (6).

* * * * *